(12) United States Patent
Nishizaki et al.

(10) Patent No.: US 9,770,458 B2
(45) Date of Patent: Sep. 26, 2017

(54) ANTI-CANCER AGENT CONTAINING A DIACYLPHOSPHATIDYLETHANOLAMINE AS AN ACTIVE INGREDIENT

(71) Applicant: NISHIZAKI BIOINFORMATION RESEARCH INSTITUTE, Hyogo (JP)

(72) Inventors: Tomoyuki Nishizaki, Hyogo (JP); Takashi Nakano, Hyogo (JP)

(73) Assignee: NISHIZAKI BIOINFORMATION RESEARCH INSTITUTE, Hyogo (JP)

( * ) Notice: Subject to any disclaimer, the term of this patent is extended or adjusted under 35 U.S.C. 154(b) by 0 days.

(21) Appl. No.: 15/106,401

(22) PCT Filed: Dec. 19, 2014

(86) PCT No.: PCT/JP2014/083657
§ 371 (c)(1),
(2) Date: Jun. 20, 2016

(87) PCT Pub. No.: WO2015/093588
PCT Pub. Date: Jun. 25, 2015

(65) Prior Publication Data
US 2017/0027968 A1    Feb. 2, 2017

(30) Foreign Application Priority Data
Dec. 21, 2013 (JP) ................... 2013-264714

(51) Int. Cl.
*A61K 31/685*    (2006.01)
(52) U.S. Cl.
CPC ................ *A61K 31/685* (2013.01)
(58) Field of Classification Search
None
See application file for complete search history.

(56) References Cited

U.S. PATENT DOCUMENTS 5,935,936 A    8/1999   Fasbender et al.

FOREIGN PATENT DOCUMENTS

| JP | 11-511757 | 10/1999 |
| JP | 2005-247728 | 9/2005 |
| WO | 2011/056682 | 5/2011 |

OTHER PUBLICATIONS

Yaguchi et al., "Dilinoleoylphosphatidylcholine ameliorates scopolamine-induced impairment of spatial learning and memory by targeting α7 nicotinic ACh receptors", Life Sciences, vol. 84, 2009, pp. 263-266.
Yaguchi et al., "1-Palmitoyl-2-oleoyl-*sn*-glycero-3-phosphocholine improves cognitive decline by enhancing long-term depression", Behavioural Brain Research, vol. 204, 2009, pp. 129-132.
International Search Report issued Mar. 24, 2015 in corresponding International Application No. PCT/JP2014/083657.
Extended European Search Report issued May 24, 2017 in European Application No. 14871776.2.
Legler et al., "Selective inhibition of CTL activation by a dipalmitoyl-phospholipid that prevents the recruitment of signaling molecules to lipid rafts", The FASEB Journal, vol. 15, No. 9, May 2001, pp. 1601-1603.
Simões et al., "Modified phosphatidylethanolamines induce different levels of cytokine expression in monocytes and dendritic cells", Chemistry and Physics of Lipids, vol. 175-176, No. 176, Aug. 2013, pp. 57-64.
Kaku et al., "Dipalmitoleoyl-phosphatidylethanolamine Induces Apoptosis of NCI-H28 Malignant Mesothelioma Cells", Anticancer Research, vol. 34, Apr. 2014, pp. 1759-1764.

*Primary Examiner* — Heidi Reese
(74) *Attorney, Agent, or Firm* — Wenderoth, Lind & Ponack, L.L.P.

(57) ABSTRACT

The present invention provides an anti-cancer agent, a cancer cell death inducing agent, a protein phosphatase 2A activation enhancing agent, a protein tyrosine phosphatase 1B activation enhancing agent and the like, each containing 1,2-dipalmitoleoyl-sn-glycero-3-phosphoethanolamine as an active ingredient.

6 Claims, 2 Drawing Sheets

ANTI-CANCER AGENT CONTAINING A DIACYLPHOSPHATIDYLETHANOLAMINE AS AN ACTIVE INGREDIENT

TECHNICAL FIELD

The present invention relates to a phospholipid compound having a cancer cell proliferation suppressive action, particularly, an anti-cancer agent containing diacylphosphatidylethanolamine as an active ingredient.

BACKGROUND ART

At present, cancer is the leading causal disease of death and a basic treatment method thereof has been demanded. For this end, many anti-cancer agents such as bleomycin, cisplatin, neocarzinostatin and the like have been developed. However, these anti-cancer agents could not provide a sufficient anti-cancer effect, since they have high toxicity and are less oriented to cancer. Therefore, various attempts have been made to make these anti-cancer agents more oriented to cancer, and one of such attempts is the development of a liposome preparation for administration of an anti-cancer agent enclosed inside the liposome. Liposome preparation is a preparation including a drug inside a particle having a bilayer membrane structure formed of phospholipid, and detailed analyses as regards cancer cell targeting have been performed.

Phospholipid is a major lipid constituting the biological membrane system, and is divided into glycerophospholipid having a glycerol skeleton, and sphingophospholipid having a sphingosine skeleton. Furthermore, depending on the kind of the hydrophilic moiety, glycerophospholipids are divided into phospholipid classes of phosphatidylcholine, phosphatidylethanolamine, phosphatidylserine, phosphatidylinositol, phosphatidylglycerol, cardiolipin, phosphatidic acid and the like.

As the functions of phospholipids, there have been reported, besides the role of a membrane-constituting component that divides cells and cell organelles, that inositol phospholipid has a known role as an intercellular signaling pathway by phospholipase C and an anchor of protein-membrane; phosphatidylserine regulates the activities of blood coagulation protein, protein kinase C and the like; sphingomyelin pathway is involved in the regulation of activity of protein kinase C and cell apoptosis; phosphatidylcholine pathway relates to the maintenance of arachidonic acid which is an inflammatory mediator and signal transduction pathway by phospholipase D; platelet-activating factor which is alkyl ether phospholipid shows platelet activation, blood vessel permeability, leukocyte migration activity; and the like, and the functions provided by the classes thereof vary widely.

For example, 1,2-dilinoleoyl-sn-glycero-3-phosphocholine and 1-palmitoyl-2-oleoyl-sn-glycero-3-phosphocholine have been reported to improve spatial learning disorder and memory disorder induced by scopolamine, or mild cognitive impairment and dementia (non-patent documents 1, 2).

Also, phosphatidylethanolamine is a phospholipid, which is one of the main components of biological membrane, and is being marketed along with phosphatidylserine and the like as health foods. Of phosphatidylethanolamines, particularly, dilinoleoyl phosphatidylethanolamine (containing two linoleic acids as fatty acids) has been reported to have cell death inducing suppressive activity, particularly, endoplasmic reticulum stress suppressive activity and, due to such activity, dilinoleoyl phosphatidylethanolamine can be used for pharmaceutical application, particularly for the prophylaxis and/or treatment of neurodegenerative disease (patent document 1).

DOCUMENT LIST

Patent Documents

Patent document 1: JP-A-2005-247728

Non-Patent Document

Non-patent document 1: Yaguchi T, Nagata T, Nishizaki T. Dilinoleoylphosphatidylcholine ameliorates scopolamine-induced impairment of spatial learning and memory by targeting alpha-7 nicotinic ACh receptors. Life Sci 2009; 84:263-6

Non-patent document 2: Yaguchi T, Nagata T, Nishizaki T. 1-Palmitoyl-2-oleoyl-sn-glycero-3-phosphocholine improves cognitive decline by enhancing long-term depression. Behav Brain Res 2009; 204:129-32

SUMMARY OF THE INVENTION

Problems to be Solved by the Invention

The present invention aims to provide an anti-cancer agent having a novel action mechanism.

Means of Solving the Problems

The present inventors have conducted intensive studies in an attempt to achieve the aforementioned object and found that phosphatidylethanolamine has a superior protein phosphatase 2A (PP2A) activation enhancing action, and a protein tyrosine phosphatase 1B (PTP1B) activation enhancing action. They have further confirmed a superior anti-cancer action of phosphatidylethanolamine having palmitic acid as fatty acid and completed the present invention. Accordingly, the present invention is as described below.

[1] An anti-cancer agent comprising 1,2-dipalmitoleoyl-sn-glycero-3-phosphoethanolamine as an active ingredient.

[2] The anti-cancer agent of the above-mentioned [1], wherein the cancer to be treated is at least one kind selected from the group consisting of glioblastoma, medulloblastoma, cancer of the tongue, pharynx cancer, laryngeal cancer, esophageal cancer, stomach cancer, colon cancer, liver cancer, gallbladder cancer, biliary tract cancer, pancreatic cancer, renal cancer, adrenal cancer, urinary bladder cancer, prostate cancer, penile cancer, uterine cancer, ovarian cancer, vulva cancer, vaginal cancer, breast cancer, thyroid cancer, lung cancer, malignant pleural mesothelioma, skin cancer, malignant melanoma, malignant bone tumor, soft tissue sarcoma, malignant lymphoma, leukemia and multiple myeloma.

[2-1] The anti-cancer agent of the above-mentioned [1], wherein the cancer to be treated is at least one kind selected from the group consisting of lung cancer, malignant pleural mesothelioma, stomach cancer, colon cancer and breast cancer.

[3] A cancer cell death inducing agent comprising 1,2-dipalmitoleoyl-sn-glycero-3-phosphoethanolamine as an active ingredient.

[4] The agent of the above-mentioned [3], wherein the cancer cell is a cell of at least one kind of cancer selected from the group consisting of glioblastoma, medulloblastoma, cancer of the tongue, pharynx cancer, laryngeal cancer, esophageal cancer, stomach cancer, colon cancer, liver cancer, gallbladder cancer, biliary tract cancer, pancreatic cancer, renal cancer, adrenal cancer, urinary bladder cancer, prostate cancer, penile cancer, uterine cancer, ovarian cancer, vulva cancer, vaginal cancer, breast cancer, thyroid cancer, lung cancer, malignant pleural mesothelioma, skin cancer, malignant melanoma, malignant bone tumor, soft tissue sarcoma, malignant lymphoma, leukemia and multiple myeloma.

[4-1] The agent of the above-mentioned [3], wherein the cancer cell is a cell of at least one kind of cancer selected from the group consisting of lung cancer, malignant pleural mesothelioma, stomach cancer, colon cancer and breast cancer.

[5] A protein phosphatase 2A activation enhancing agent comprising 1,2-dipalmitoleoyl-sn-glycero-3-phosphoethanolamine as an active ingredient.

[6] A protein tyrosine phosphatase 1B activation enhancing agent comprising 1,2-dipalmitoleoyl-sn-glycero-3-phosphoethanolamine as an active ingredient.

[7] The agent of the above-mentioned [5] or [6], which is an anti-cancer agent.

[8] The agent of the above-mentioned [5] or [6], which is a reagent for research.

[9] A method for the prophylaxis and/or treatment of cancer, comprising administering an effective amount of 1,2-dipalmitoleoyl-sn-glycero-3-phosphoethanolamine to a subject in need thereof.

[10] The method of the above-mentioned [9], wherein the cancer is at least one kind selected from the group consisting of glioblastoma, medulloblastoma, cancer of the tongue, pharynx cancer, laryngeal cancer, esophageal cancer, stomach cancer, colon cancer, liver cancer, gallbladder cancer, biliary tract cancer, pancreatic cancer, renal cancer, adrenal cancer, urinary bladder cancer, prostate cancer, penile cancer, uterine cancer, ovarian cancer, vulva cancer, vaginal cancer, breast cancer, thyroid cancer, lung cancer, malignant pleural mesothelioma, skin cancer, malignant melanoma, malignant bone tumor, soft tissue sarcoma, malignant lymphoma, leukemia and multiple myeloma.

[10-1] The method of the above-mentioned [10], wherein the cancer is at least one kind selected from the group consisting of lung cancer, malignant pleural mesothelioma, stomach cancer, colon cancer and breast cancer.

[11] A method of inducing cell death of a cancer cell, comprising treating cancer cell with 1,2-dipalmitoleoyl-sn-glycero-3-phosphoethanolamine.

[12] The method of the above-mentioned [11], wherein the cancer cell is at least one kind of cancer selected from the group consisting of glioblastoma, medulloblastoma, cancer of the tongue, pharynx cancer, laryngeal cancer, esophageal cancer, stomach cancer, colon cancer, liver cancer, gallbladder cancer, biliary tract cancer, pancreatic cancer, renal cancer, adrenal cancer, urinary bladder cancer, prostate cancer, penile cancer, uterine cancer, ovarian cancer, vulva cancer, vaginal cancer, breast cancer, thyroid cancer, lung cancer, malignant pleural mesothelioma, skin cancer, malignant melanoma, malignant bone tumor, soft tissue sarcoma, malignant lymphoma, leukemia and multiple myeloma.

[12-1] The method of the above-mentioned [11], wherein the cancer cell is a cell of at least one kind of cancer selected from the group consisting of lung cancer, malignant pleural mesothelioma, stomach cancer, colon cancer and breast cancer.

[13] 1,2-Dipalmitoleoyl-sn-glycero-3-phosphoethanolamine for use in the prophylaxis and/or treatment of cancer.

[14] 1,2-Dipalmitoleoyl-sn-glycero-3-phosphoethanolamine of the above-mentioned [13], wherein the cancer is at least one kind selected from the group consisting of glioblastoma, medulloblastoma, cancer of the tongue, pharynx cancer, laryngeal cancer, esophageal cancer, stomach cancer, colon cancer, liver cancer, gallbladder cancer, biliary tract cancer, pancreatic cancer, renal cancer, adrenal cancer, urinary bladder cancer, prostate cancer, penile cancer, uterine cancer, ovarian cancer, vulva cancer, vaginal cancer, breast cancer, thyroid cancer, lung cancer, malignant pleural mesothelioma, skin cancer, malignant melanoma, malignant bone tumor, soft tissue sarcoma, malignant lymphoma, leukemia and multiple myeloma.

[14-1] 1,2-Dipalmitoleoyl-sn-glycero-3-phosphoethanolamine of the above-mentioned [13], wherein the cancer is at least one kind selected from the group consisting of lung cancer, malignant pleural mesothelioma, stomach cancer, colon cancer and breast cancer.

Effect of the Invention

Phosphatidylethanolamine, particularly, phosphatidylethanolamine having palmitic acid as a constituent fatty acid, has a superior cancer cell death inducing action. Phospholipid compounds such as phosphatidylethanolamine and the like are inherently present in living organisms. Therefore, the present invention can provide an anti-cancer agent more superior in safety.

DESCRIPTION OF EMBODIMENTS

The present invention is explained in detail below.

In the present invention, phosphatidylethanolamine is used as the active ingredient. Of the phosphatidylethanolamines used in the present invention as the active ingredient, preferred is 1,2-dipalmitoleoyl-sn-glycero-3-phosphoethanolamine (DPPE), and an anti-cancer agent containing phosphatidylethanolamine as an active ingredient is provided. DPPE is also referred to as dipalmitoleoyl.phosphatidylethanolamine.

Phospholipid is largely divided into two: glycerophospholipid having glycerol as the skeleton, and sphingophospholipid having sphingosine as the skeleton. It has a structure wherein glycerol or sphingosine is the central skeleton, two fatty acids and phosphoric acid are bonded thereto, and alcohol is ester-bonded to phosphoric acid. DPPE is a glycerophospholipid, wherein two fatty acids bound to glycerol to be the central skeleton are palmitic acids, and alcohol ester-bound to phosphoric acid is ethanolamine.

It should be noted that DPPE may contain one or more stereoisomers (e.g., optical isomer, geometric isomer) due to an asymmetric carbon atom or a double bond, and all of such isomers and mixtures thereof are encompassed within the scope of the present invention.

DPPE can be produced according to a general synthesis method of phosphatidylethanolamine. In addition, DPPE is commercially available and preferably used conveniently.

DPPE may also be used in the form of a salt thereof. Such salt is not particularly limited, and a salt acceptable as a medicament or food is preferable. Examples thereof include salts with inorganic base (e.g., alkali metal such as sodium, potassium and the like; alkaline earth metal such as calcium, magnesium and the like; aluminum, ammonium), organic base (e.g., trimethylamine, triethylamine, pyridine, picoline, ethanolamine, diethanolamine, triethanolamine, dicyclohexylamine, N,N-dibenzylethylenediamine), inorganic acid (e.g., hydrochloric acid, hydrobromic acid, nitric acid, sulfuric acid, phosphoric acid), organic acid (e.g., formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid), basic amino acid (e.g., arginine, lysine, ornithine) or acidic amino acid (e.g., aspartic acid, glutamic acid) and the like.

Figure 2:
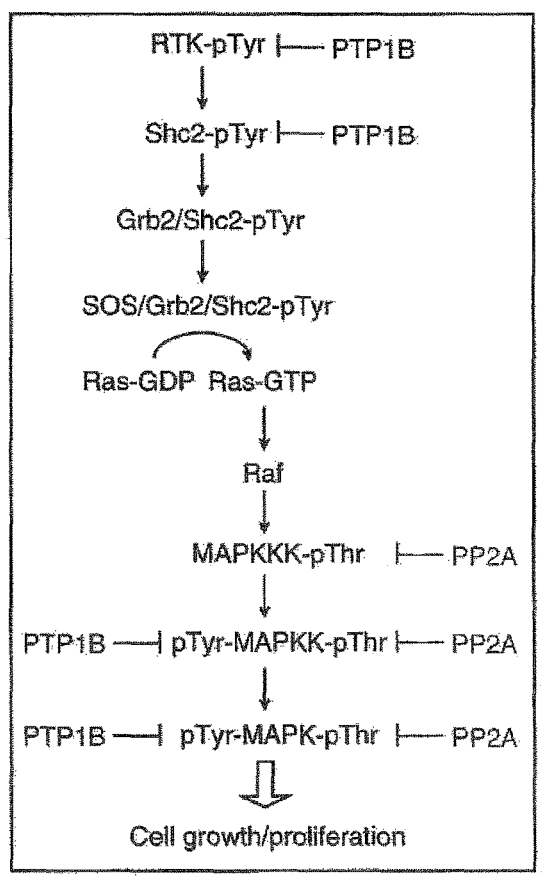
FIG. 2 is a scheme schematically showing the action sites of PP2A and PTP1B in cell proliferation. RTK: receptor tyrosine kinase, MAPK: mitogen-activated protein kinase, MAPKK: mitogen-activated protein kinase kinase, MAPKKK: mitogen-activated protein kinase kinase kinase, GDP: guanosine diphosphate, GTP: guanosine triphosphate

DPPE has, as shown by the data in Examples, (1) protein phosphatase 2A (PP2A) activation enhancing action, and (2) protein tyrosine phosphatase 1B (PTP1B) activation enhancing action. With these superior pharmacological actions, it induces a growth suppressive action on cancer cells, and can be provided as pharmaceutical products such as an anti-cancer agent and the like. FIG. 2 shows the point of action of PP2A and PTP1B in the cell proliferation pathway. Since it potentiates PP2A activation and/or potentiates PTP1B activation, it can inhibit, in each stage, phosphorylation-caused activation of factors at downstream, whereby the growth of cancer cell can be suppressed.

The pharmacological actions of DPPE clarified in the present invention are the following.

(1) PP2A Activation Enhancing Action

Protein phosphatase 2A (PP2A) is one kind of serine/threonine phosphatase, and plays an important role in the signal transduction in vivo which is involved in the intracellular processing such as cell cycle, growth, differentiation and the like.

PP2A has an action to dephosphorylate p53, c-Myc, b-Catenin besides Akt, MEK, ERK, and is known to also function as a cell proliferation, signal transduction or apoptosis regulating factor.

Reference document: P. Seshacharyulu P et al., Phosphatase: PP2A structural importance, regulation and its aberrant expression in cancer. Cancer Lett 2013; 335:9-18.

Therefore, a PP2A activation enhancing agent may be possibly applied to various pharmaceutical uses.

(2) PTP1B Activation Enhancing Action

Protein tyrosine phosphatase (PTP) 1B is a cytosolic tyrosine phosphatase, and involved in the regulation of tyrosine kinase since it controls the phosphorylation state of tyrosine kinase.

It is known that PTP1B has an action to control cell proliferation, differentiation, apoptosis, and cell migration (chemotaxis).

Reference document: Haj F G et al., Regulation of receptor tyrosine kinase signaling by protein tyrosine phosphatase-1B. J Biol Chem 2003; 278:739-744.

Therefore, a PTP1B activation enhancing agent may be possibly applied to various pharmaceutical uses.

Furthermore, DPPE has an action to induce cell death of various cancer cells and suppress cell proliferation, as shown in the data of the Examples. Such pharmacological action shows that DPPE is useful as a cancer cell death-inducing agent (hereinafter to be simply referred to as the agent of the present invention), and also useful as a reagent for study which can be a tool useful for the development of an anti-cancer agent or a prophylactic or therapeutic drug for cancer (hereinafter to be simply referred to as the medicament of the present invention).

Moreover, by the pharmacological action of DPPE, the present invention can provide a method of inducing the cell death of cancer cells, and a prophylactic and/or treatment method of cancer (hereinafter to be simply referred to as the method of the present invention).

When used in the present specification, the test subject (target) may be a mammal. Examples of the mammal include primates (e.g., human, monkey, chimpanzee), rodents (e.g., mouse, rat, guinea pig), pets (e.g., dog, cat, rabbit), working animals or domestic animals (e.g., bovine, horse, swine, sheep, goat), and human is preferable.

The cancer (cancer cell) to which the agent, medicament or method of the present invention is applied is not particularly limited, and specific examples thereof include glioblastoma, medulloblastoma, cancer of the tongue, pharynx cancer, laryngeal cancer, esophageal cancer, stomach cancer, colon cancer, liver cancer, gallbladder cancer, biliary tract cancer, pancreatic cancer, renal cancer, adrenal cancer, urinary bladder cancer, prostate cancer, penile cancer, uterine cancer, ovarian cancer, vulva cancer, vaginal cancer, breast cancer, thyroid cancer, lung cancer, malignant pleural mesothelioma, skin cancer, malignant melanoma, malignant bone tumor, soft tissue sarcoma, malignant lymphoma, leukemia, multiple myeloma and the like. Preferably, they are applied to malignant pleural mesothelioma, lung cancer, stomach cancer, colon cancer and breast cancer.

Similarly, when used in the present specification, the target cancer cells to be treated by DPPE are various cancer cells to which the above-mentioned medicament of the present invention is applied, and specific examples thereof include glioblastoma, medulloblastoma, cancer of the tongue, pharynx cancer, laryngeal cancer, esophageal cancer, stomach cancer, colon cancer, liver cancer, gallbladder cancer, biliary tract cancer, pancreatic cancer, renal cancer, adrenal cancer, urinary bladder cancer, prostate cancer, penile cancer, uterine cancer, ovarian cancer, vulva cancer, vaginal cancer, breast cancer, thyroid cancer, lung cancer, malignant pleural mesothelioma, skin cancer, malignant melanoma, malignant bone tumor, soft tissue sarcoma, malignant lymphoma, leukemia, multiple myeloma and the like. Preferably, they are applied to malignant pleural mesothelioma, lung cancer, stomach cancer, colon cancer and breast cancer.

The "treatment" here means bringing the above-mentioned cells into contact with DPPE for a necessary and sufficient time. While the time varies depending on the desired effect and the kind of the cells to be used, it is generally 0.5-76 hr, preferably about 0.5-48 hr. Alternatively, the treatment may be performed for a shorter time, for example, about 0.5-24 hr, preferably about 0.5-12 hr. Conveniently, it is performed by culturing in a culture medium containing DPPE.

While the dose of the medicament of the present invention varies depending on the kind of cancer of the administration subject, severity thereof, animal species to be the administration subject, drug acceptability, body weight, age and the like of the administration subject, by an oral or parenteral route, generally, 0.1-10 g, preferably 1-4 g, in the amount of DPPE as the active ingredient is administered per day to an adult subject by oral administration, and 0.01 g-1 g, preferably 0.1-0.4 g, by parenteral administration.

The medicament of the present invention can contain, besides DPPE which is the active ingredient, any additive, for example, a pharmaceutically acceptable carrier. Examples of the pharmaceutically acceptable carrier include, but are not limited to, excipients such as sucrose, starch, mannit, sorbit, lactose, glucose, cellulose, talc, calcium phosphate, calcium carbonate and the like, binders such as cellulose, methylcellulose, hydroxypropylcellulose, polypropylpyrrolidone, gelatin, gum arabic, polyethylene glycol, sucrose, starch and the like, disintegrants such as starch, carboxymethylcellulose, hydroxypropylstarch, sodium-glycol-starch, sodium hydrogen carbonate, calcium phosphate, calcium citrate and the like, lubricants such as magnesium stearate, aerosil, talc, sodium lauryl sulfate and the like, aromatic substances such as citric acid, menthol, glycyllysine ammonium salt, glycine, orange powder and the like, preservatives such as sodium benzoate, sodium bisulfite, methylparaben, propylparaben and the like, stabilizers such as citric acid, sodium citrate, acetic acid and the like, suspensions such as methylcellulose, polyvinylpyrrolidone, aluminum stearate and the like, dispersing agents such as surfactant and the like, diluents such as water, saline, orange juice and the like, base waxes such as cacao butter, polyethylene glycol, kerosene and the like, and the like.

In one embodiment, the medicament of the present invention can be formulated as a preparation preferable for oral administration. Examples of the preparation preferable for oral administration include a liquid wherein an effective amount of a substance is dissolved in a diluent such as water and saline, a capsule, granule, powder or tablet containing an effective amount of a substance as a solid or granules, a suspension wherein an effective amount of a substance is suspended in a suitable dispersion medium, an emulsion wherein a solution of an effective amount of a substance is dispersed and emulsified in a suitable dispersion medium, and the like.

In another embodiment, the medicament of the present invention can be formulated as a preparation preferable for parenteral administration. Examples of the preparation preferable for parenteral administration (e.g., intravenous injection, subcutaneous injection, muscular injection, topical injection and the like) include aqueous and nonaqueous isotonic aseptic injection liquids, which may contain antioxidant, buffer, bacteriostatic, isotonicity agent and the like. In addition, examples thereof include aqueous and nonaqueous aseptic suspensions, which may contain suspension, solubilizer, thickener, stabilizer, preservative and the like. Unit dose or plural doses of the preparation can be filled in a container such as ampoule and vial. Moreover, the active ingredient and a pharmaceutically acceptable carrier can be freeze-dried and preserved in a form that can be dissolved or suspended in a suitable aseptic vehicle immediately before use.

The medicament of the present invention may be packed or filled individually by a unit ingestion amount or a divided amount thereof, or packed or filled comprehensively by many unit ingestion amounts or divided amounts thereof.

Examples of the medicament wherein a unit ingestion amount or a divided amount thereof is packed or filled individually include general packages (e.g., PTP (press through packing) sheet, paper container, film (e.g., plastic film) container, glass container, plastic container) packed or filled with the unit ingestion amount or a divided amount thereof. The medicaments that are individually packed or filled may be further combined and packed or filled in a single container (e.g., paper container, film (e.g., plastic film) container, glass container, plastic container). Examples of the medicament wherein many unit ingestion amounts or a divided amount thereof are/is comprehensively packed or filled include those wherein many tablets or capsules are packed or filled in a single container (e.g., paper container, film (e.g., plastic film) container, glass container, plastic container) without distinction. The medicament of the present invention may contain a unit ingestion amount or a divided amount thereof in a number sufficient for long-term ingestion. For example, a food can contain same in a number sufficient for ingestion for not less than 3 days, preferably not less than 7 days, 10 days, 14 days or 21 days, or 1 month, 2 months, or not less than 3 months.

The medicament of the present invention may contain, besides DPPE to be the essential active ingredient, one or more kinds of other anti-cancer agents. Examples of other anti-cancer agent include metabolic antagonist (e.g., methotrexate, 5-fluorouracil etc.), alkylating agent (e.g., cyclophosphamide, ifosfamide etc.), platinum anti-cancer agent (e.g., cisplatin, carboplatin etc.), topoisomerase inhibitor (e.g., etoposide etc.), anticancer antibiotics (e.g., mitomycin, adriamycin etc.), plant-derived anticancer agent (e.g., vincristine, vindesine, taxol etc.), tyrosine kinase inhibitor (e.g., gefinitib, imanitib etc.), humanized antibody (e.g., herceptin etc.) and the like.

The contents disclosed in any publication cited in the present specification, including patents and patent applications, are hereby incorporated in their entireties by reference, to the extent that they have been disclosed herein.

While the present invention is explained in more detail in the following by referring to Examples, the present invention is not at all limited by the following Examples and the like.

EXAMPLES

Example 1

PP2A Activation Enhancing Action and PTP1B Activation Enhancing Action

Method

1. Assay of PP2A and PTP1B Activities Under Cell-Free Conditions

The measurement of PP2A and PTP1B under cell-free conditions was performed according to the method described in a previous report (Kanno T et al., Cell Physiol Biochem 2012; 30:1014-1022.). Human recombinant PP2A was purchased from Millipore (Billerica, Mass., USA). Human PTP1B was cloned to pGEX-6P-3 vector having a GST tag on the $NH_2$ terminal, and expressed in competent *E. coli* 3L21 (DE3) suitable for transformation and protein expression. GST fused PTP1B was affinity-purified using glutathione sepharose 4B (GE Healthcare Bio-Science KK, Tokyo, Japan). They were reacted with p-nitrophenylphosphate (p-NPP) (Sigma, St. Louis, Mo., USA) as a substrate, and each phosphatase activity was measured. PP2A (0.2 U/well) or PTP1B (1 mg/well) was preincubated in a reaction medium at 37° C. for 30 min. in the presence and absence of a phosphatase inhibitor (okadaic acid; 2 nM, sodium vanadate; 1 µM) and, phosphatidylethanolamine (DAPE, DLPE, DOPE, DPPE; 100 µM, all obtained from Avanti Polar Lipids, Inc. (Alabaster, Ala., USA)).

reaction medium for PP2A: 50 mM Tris-HCl, 0.1 mM EGTA, 0.1% (v/v) 2-mercaptoethanol, pH 7.0 reaction medium for PTP1B: 50 mM HEPES, 1 mM EDTA, 50 mM NaCl, 1 mM dithiothreitol, pH 7.2

Then, p-NPP (0.5 mM for PP2A, 10 mM for PTP1B) was added to the reaction medium and incubation was continued for 60 min. The reaction was discontinued by adding 0.1N NaOH. Dephosphorylated p-NPP, namely, p-NP, was quantified at absorbance 405 nm by using SpectraMax PLUS384 (Molecular Devices, Sunnyvale, Calif., USA).

Results

Figure 1:
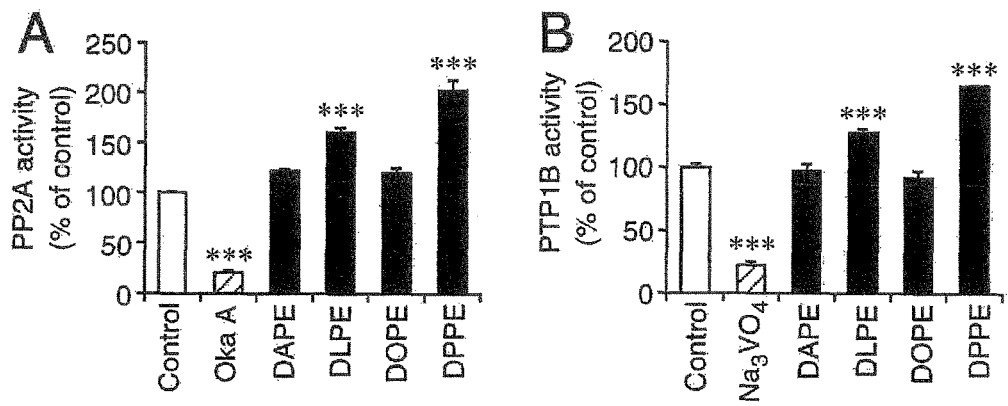
FIG. 1 is a graph showing an influence of various phosphatidylethanolamines on the activity of protein phosphatase 2A (PP2A) and protein tyrosine phosphatase 1B (PTP1B). A shows the results of PP2A, and B shows the results of PTP1B. The vertical axis shows the activity of each phosphatase. DAPE: 1,2-diarachidonoyl-sn-glycero-3-phosphoethanolamine, DLPE: 1,2-dilinoleoyl-sn-glycero-3-phosphoethanolamine, DOPE: 1,2-dioleoyl-sn-glycero-3-phosphoethanolamine, DPPE: 1,2-dipalmitoleoyl-sn-glycero-3-phosphoethanolamine, Oka A: okadaic acid. In the graph, each value shows mean (±SEM) percentage relative to the phosphatase activity to be the base of the control free of a drug treatment (n=4 in each experiment). ***$P<0.0001$ (relative to control), Dunnett's test.

The results are shown in FIG. 1. The results indicate that DPPE has a strong PP2A activation enhancing action and a PTP1B activation enhancing action. In light of the signal pathway of cell proliferation shown in FIG. 2, such actions of DPPE suggest that it suppresses cell proliferation.

Example 2

Cancer Cell Death Inducing Action

Material and Method

1. Cell Culture

NCI-H28 which is a cell line of human malignant pleural mesothelioma and Met5A which is a cell line of human non-malignant mesothelioma were used. These cells were purchased from American Type Culture Collection (Manassas, Va., USA). The cells were cultured in Roswell Park Memorial Institute (RPMI)-1640 medium added with 0.003% (w/v) L-glutamine. The cells were incubated in a medium added with 10% (v/v) heat-inactivated bovine serum, penicillin (final concentration, 100 U/ml) and streptomycin (final concentration, 0.1 mg/ml) in a humid environment under 5% $CO_2$ and 95% air at 37° C.

2. Cell Viability Assay

The cell viability was evaluated according to previous report (Nogi Y, et al., Cell Physiol Biochem 2012; 30: 61-74.) by using 3-(4,5-dimethyl-2-thiazolyl)-2,5-diphenyl-2H-tetrazolium bromide (MTT). The measurement was performed by treating Met5A (human non-malignant mesothelioma cell) and NCI-H28 (human malignant mesothelioma cell) for 24 hr or 48 hr while changing the concentration of DPPE to 0, 1 µM, 10 µM and 100 µM.

3. TUNEL (Terminal Deoxynucleotidyl Transferase-Mediated dUTP Nick End Labeling) Staining To detect in situ DNA fragmentation to be the index of apoptosis, TUNEL staining was performed using In Situ Apoptosis Detection Kit (Takara Bio; Otsu, Japan). The cells fixed and membrane-permeabilized were incubated with terminal deoxynucleotidyl transferase and fluorescein isothiocyanate (FITC)-deoxyuridinetriphosphate at 37° C. for 90 min. FITC signal was visualized by a confocal laser microscope (LSM 510; Carl Zeiss Co., Ltd., Oberkochen, Germany).

The cells used were Met5A (human non-malignant mesothelioma cell) and NCI-H28 (human malignant mesothelioma cell), after a treatment for 48 hr by changing the concentration of DPPE to 0, 30 µM and 100 µM.

Results

Figure 3:
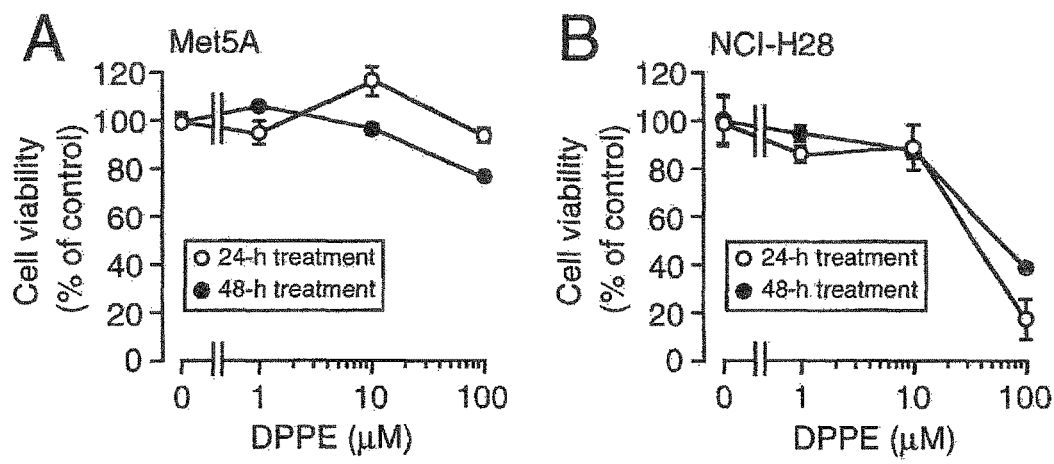
FIG. 3 is a graph showing that 1,2-dipalmitoleoyl-sn-glycero-3-phosphoethanolamine (DPPE) induces cell death of human malignant pleural mesothelioma in a concentration-dependent manner. A shows the results of a human non-malignant mesothelioma cell, Met5A, and B shows the results of a human malignant mesothelioma cell, NCI-H28. ○ shows the results after treatment for 24 hr, and ● shows the results after treatment for 48 hr. The vertical axis shows cell survival rate, and the horizontal axis shows the concentration of DPPE. In the graph, each point shows mean (±SD) percentage relative to the MTT intensity of a cell free of a DPPE treatment (n=4 in each experiment).
Figure 4:
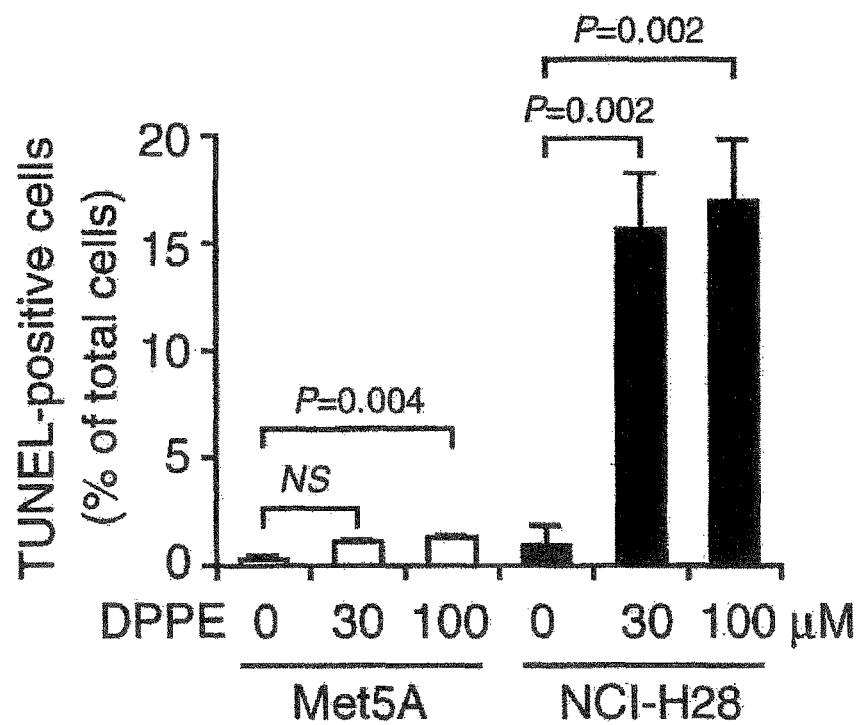
FIG. 4 is a graph showing that DPPE induces apoptosis of human malignant pleural mesothelioma cells. The vertical axis shows the proportion of the TUNEL-stained cells relative to the total cells, and the horizontal axis shows the concentration of DPPE. In the graph, each column shows mean (±SD) percentage of the TUNEL-stained cells relative to the total cells (n=4 in each experiment). P value was determined by Dunnett's test.

The results of the assay of cell survival rate are shown in FIG. 3, and the results of the TUNEL staining are shown in FIG. 4. From the results of FIG. 3, it is clear that DPPE is almost uninfluential on the non-malignant mesothelioma cell, but induces concentration-dependent cell death in the malignant mesothelioma cell. Furthermore, from the results of FIG. 4, it is clear that DPPE induces apoptosis of the malignant mesothelioma cell but does not induce apoptosis of the non-malignant mesothelioma cell.

INDUSTRIAL APPLICABILITY

Since DPPE has a strong PP2A activation enhancing action and a strong PTP1B activation enhancing action, and further, a superior cancer cell death inducing action, it is expected to be applicable as an anti-cancer agent. Since phospholipid compounds are inherently present in the living body, the present invention can provide an anti-cancer agent more superior in safety.

This application is based on a patent application No. 2013-264714 filed in Japan (filing date: Dec. 21, 2013), the contents of which are incorporated in full herein.

The invention claimed is:

1. A method for the treatment of cancer, comprising administering an effective amount of 1,2-dipalmitoleoyl-sn-glycero-3-phosphoethanolamine to a subject in need thereof.

2. The method according to claim 1, wherein the cancer is at least one kind selected from the group consisting of glioblastoma, medulloblastoma, cancer of the tongue, pharynx cancer, laryngeal cancer, esophageal cancer, stomach cancer, colon cancer, liver cancer, gallbladder cancer, biliary tract cancer, pancreatic cancer, renal cancer, adrenal cancer, urinary bladder cancer, prostate cancer, penile cancer, uterine cancer, ovarian cancer, vulva cancer, vaginal cancer, breast cancer, thyroid cancer, lung cancer, malignant pleural mesothelioma, skin cancer, malignant melanoma, malignant bone tumor, soft tissue sarcoma, malignant lymphoma, leukemia and multiple myeloma.

3. A method of inducing cell death of a cancer cell, comprising treating cancer cell with 1,2-dipalmitoleoyl-sn-glycero-3-phosphoethanolamine.

4. The method according to claim 3, wherein the cancer cell is at least one kind of cancer selected from the group consisting of glioblastoma, medulloblastoma, cancer of the tongue, pharynx cancer, laryngeal cancer, esophageal cancer, stomach cancer, colon cancer, liver cancer, gallbladder cancer, biliary tract cancer, pancreatic cancer, renal cancer, adrenal cancer, urinary bladder cancer, prostate cancer, penile cancer, uterine cancer, ovarian cancer, vulva cancer, vaginal cancer, breast cancer, thyroid cancer, lung cancer, malignant pleural mesothelioma, skin cancer, malignant melanoma, malignant bone tumor, soft tissue sarcoma, malignant lymphoma, leukemia and multiple myeloma.

5. The method according to claim 1, wherein the cancer is at least one kind selected from the group consisting of lung cancer, malignant pleural mesothelioma, skin cancer, malignant melanoma, malignant bone tumor, soft tissue sarcoma, malignant lymphoma, leukemia and multiple myeloma.

6. The method according to claim 3, wherein the cancer cell is at least one kind of cancer selected from the group consisting of lung cancer, malignant pleural mesothelioma, skin cancer, malignant melanoma, malignant bone tumor, soft tissue sarcoma, malignant lymphoma, leukemia and multiple myeloma.

\* \* \* \* \*